United States Patent [19]

Gregorig et al.

[11] Patent Number: 4,674,879
[45] Date of Patent: Jun. 23, 1987

[54] DETECTING OIL IN WATER

[75] Inventors: Stephen I. N. Gregorig, Crawley; John O. Parry, Prestatyn, both of United Kingdom

[73] Assignee: STC,PLC, London, England

[21] Appl. No.: 791,338

[22] Filed: Oct. 25, 1985

[30] Foreign Application Priority Data

Oct. 27, 1984 [GB] United Kingdom ............... 8427208

[51] Int. Cl.$^4$ ............................................. G01J 3/44
[52] U.S. Cl. .................................... 356/301; 356/345
[58] Field of Search ............... 250/255, 301, 341, 343, 250/345; 356/70

[56] References Cited

FOREIGN PATENT DOCUMENTS 1556029 11/1979 United Kingdom .
1602969 11/1981 United Kingdom .
2097529 11/1982 United Kingdom .

Primary Examiner—Eugene R. LaRoche
Assistant Examiner—Robert J. Pascal
Attorney, Agent, or Firm—Kerkam, Stowell Kondracki & Clarke

[57] ABSTRACT

Oil concentration levels in water are measured by a light scattering/absorption technique. The intensity of directly transmitted and scattered light signals are compared to provide a correction factor corresponding to the level of solid contaminents in the mixture. This correction factor is then applied to a signal corresponding to the intensity of light transmitted directly through the mixture to provide an accurate oil concentration measurement.

4 Claims, 7 Drawing Figures

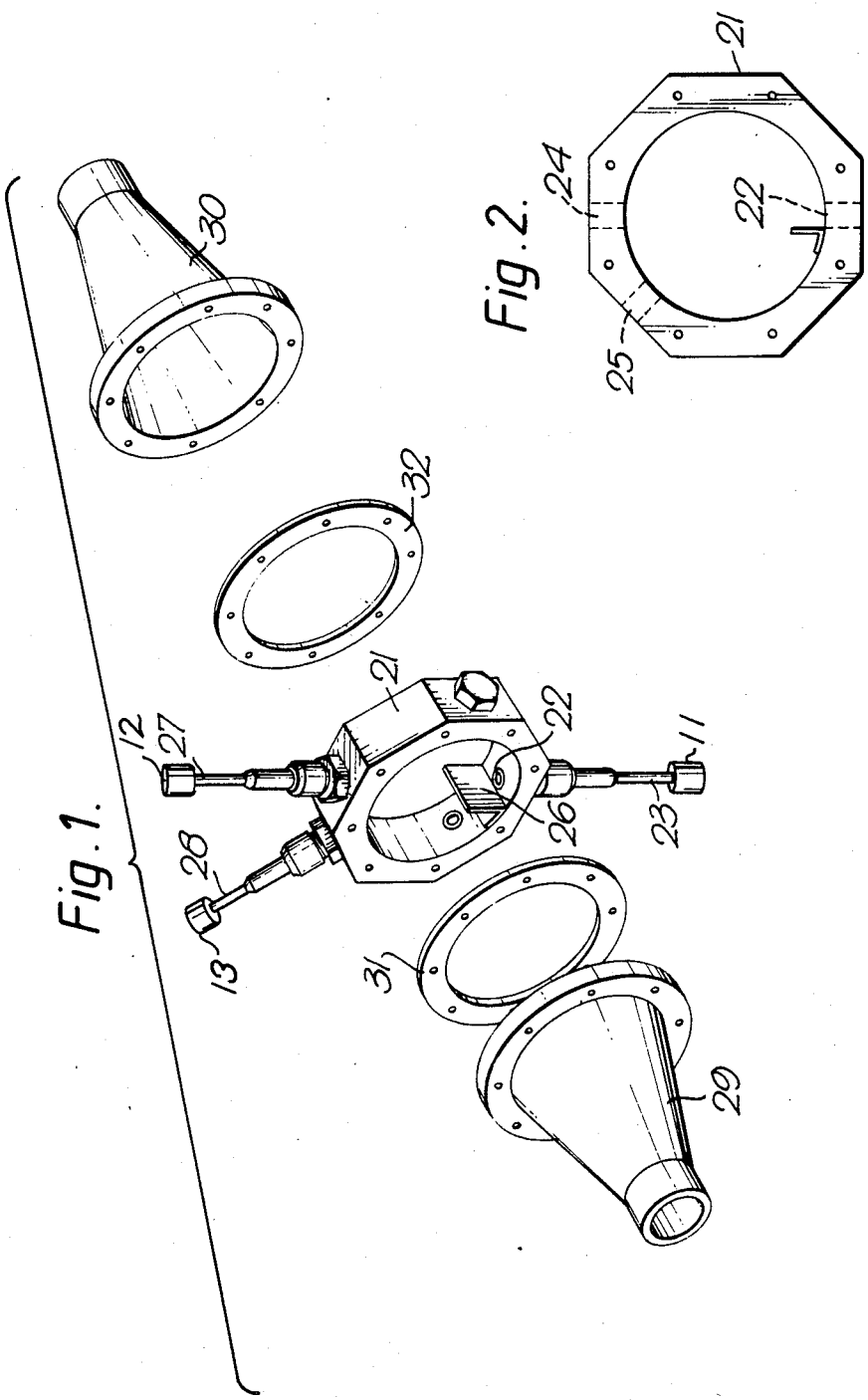

DETECTING OIL IN WATER

This invention relates to an apparatus and method for detecting oil in water e.g. for use on a mariner vessel.

BACKGROUND OF THE INVENTION

One of the problems involved in the detection and measurement of small traces of oil in water using a light scattering technique is that of differentiating between oil droplets and suspended solid particles. This problem is particularly acute in a marine environment where water almost invariably contains particles of rust released from ferrous metal surfaces. In a conventional oil-in-water detector the intensity of light scattered at an angle to an incident light beam is measured and an oil level reading is derived directly from this intensity. It will be appreciated that the presence of suspended solid particles in the water can, at low oil levels, lead to widely inaccurate results. In an attempt to overcome this problem the use of a plurality of photodetectors each arranged at a different scattering angle to an incident light beam has been proposed. Since the angular scattering characteristics of oils and solids are different it is possible to extract from the outputs of the various detectors a measure of the oil level. Such an arrangement however is relatively costly and cannot readily be fitted to those existing installations which employ a single scattering angle for the detection process.

The object of the invention is to minimize or to overcome this disadvantage.

SUMMARY OF THE INVENTION

According to one aspect of the invention there is provided a method of detecting and measuring oil dispersed in water, the method including directing a substantially monochromatic light beam through an oil/water mixture, measuring the relative intensities of light transmitted directly through the mixture and scattered at an angle to the incident beam, and normalizing the direct and transmitted output signals by multiplying said signals by respective first and second predetermined multiplication factors, comparing the two normalized output signals, and subtracting from the normalized scatter output signal a further factor proportional to the difference between the two normalized output signals thereby obtaining a measure of the oil concentration in the mixture.

According to another aspect of the invention there is provided an apparatus for detecting and measuring oil in water, the apparatus including a cell through which an oil/water mixture may be directed, means for directing a substantially monochromatic light beam through the cell, means for detecting the intensity of light transmitted via direct and scatter paths through the cell and for generating voltage signals corresponding to said intensities, and means for calculating from said voltages a correction factor corresponding to the level of non-oleus contamination in the oil water mixture and for applying said factor to the direct path voltage signal thereby providing a measure of the oil concentration in the mixture.

The correction factor may be calculated using the difference between the oil concentration values derived from the direct and scatter signals. This factor may then be applied to the direct concentration value.

BRIEF DESCRIPTION OF THE DRAWINGS

An embodiment of the invention will now be described with reference to the accompanying drawings in which:

FIG. 1 is an exploded diagram of an oil detector light scatter cell;

FIG. 2 is a cross-sectional view of the cell of FIG. 1;

DESCRIPTION OF PREFERRED EMBODIMENT

Figure 7:
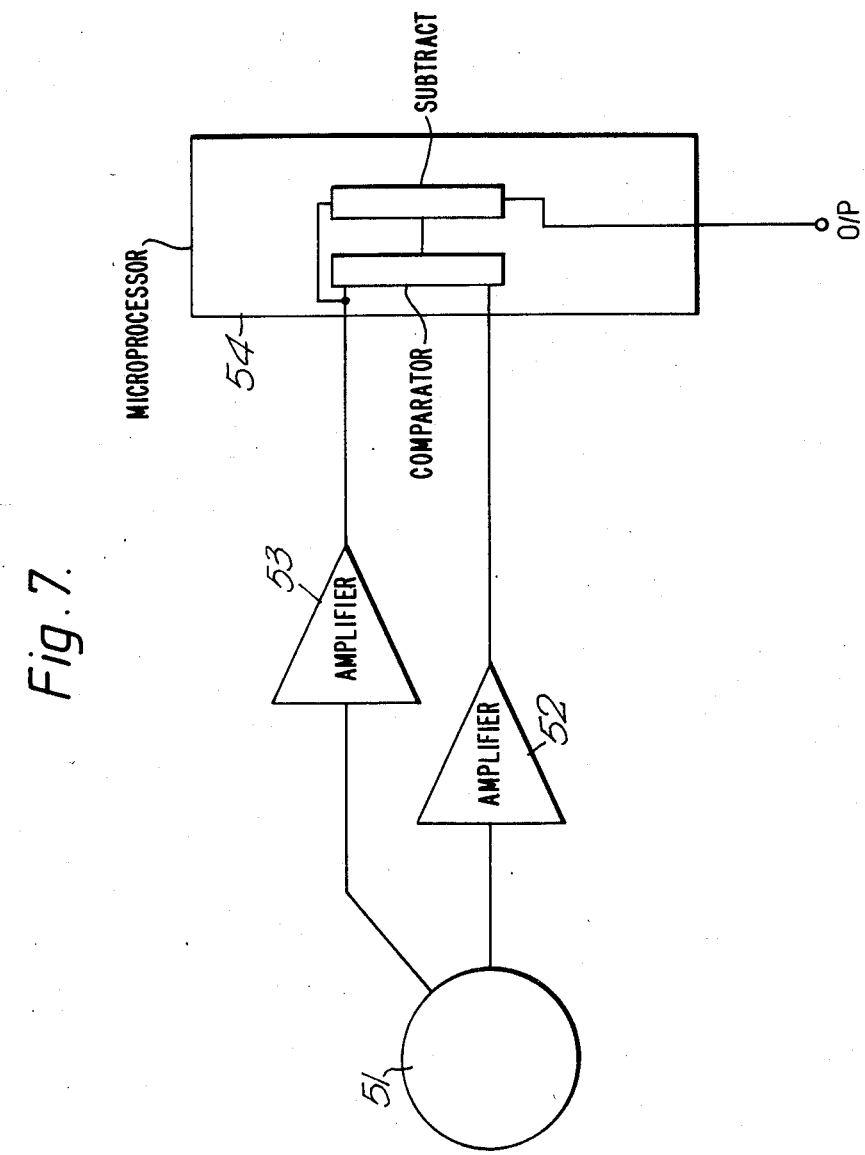
FIG. 7 is a schematic diagram of an apparatus for performing the signal processing of oil level measurements.

Referring to FIGS. 1 and 2, and 7, the scatter cell includes a central body member 21 through which, in use, water containing oil is directed. The body 21 has an input window 22 whereby substantially monochromatic light, e.g. from a semiconductor laser 11) is directed into the cell preferably via an optical fibre 23 coupled to the window 22. Light is received from the cell via output windows 24 and 25, these windows being radially radically disposed relative to the input window 22 so as to receive directly transmitted light and scattered light respectively. The scatter angle may be chosen to maximize the sensitivity of the cell. Typically it is in the range 15° to 45° . A baffle 26 may be provided adjacent the input window 22 to shield the scatter output window 25 from spurious signals. The output signals from the cell may be transmitted to first and second photodetectors 12, 13 via respective optical fibres 27 and 28. In use water is directed through the body member 21 via first and second conical members (29, 30) sealed to the cell by gaskets (31, 32). The smaller diameter ends of the conical members are each adapted to receive a water pipe whereby water is directed through the cell.

Light signals received at the windows 24 and 25 via direct and scatter paths are processed in the following way. The signals are fed each to a respective photodetectors 12, 13 and the resultant electrical signals are amplified by respective amplifiers 52, 53 (FIG. 7) to provide direct and scatter output signal voltages $V_d$ and $V_s$ respectively. The amplification factor applied to each signal is chosen such that, in the absence of solid particles, the oil concentration values derived from the amplified direct and scatter signals are substantially equal. The relative amplification factors of the two signals may be determined by computation or experiment. Preferably the factors are determined from the direct response with clean water.

Figure 3:
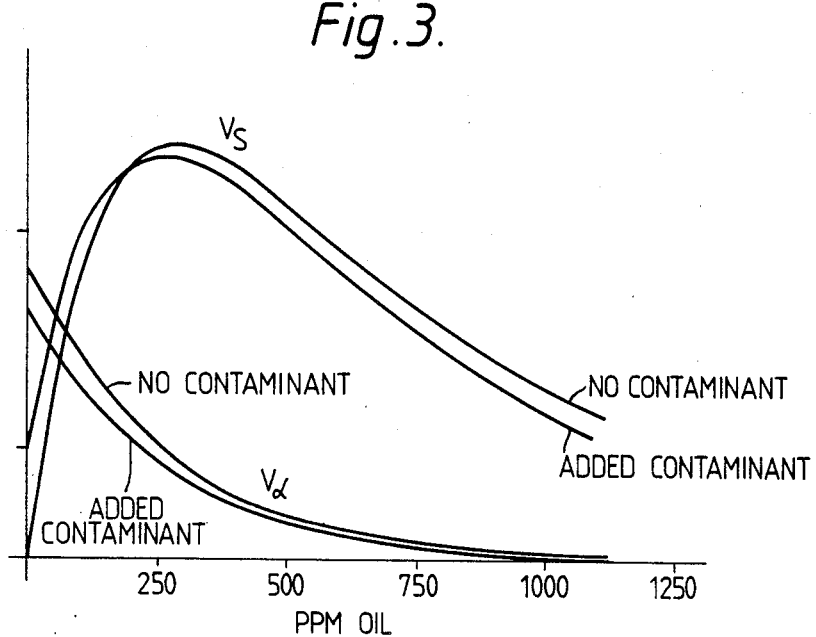
FIGS. 3 and 4 illustrate the effect of contaminent on oil readings.
Figure 4:
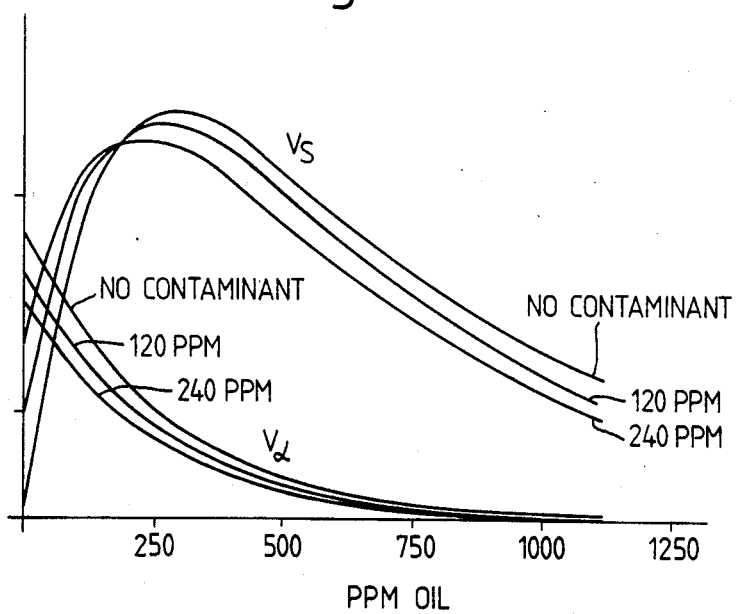

The effect of contaminent on oil readings is substantially linear up to approximately 500 ppm oil. This is illustrated in FIG. 3 of the accompanying drawings which shows direct and scatter oil level responses for both clean and contaminated oil/water mixtures. Similarly, FIG. 4 illustrates the essentially linear effect of increasing contaminant levels on the apparent oil level.

We have found that the direct output signal $V_d$ and the scatter output signal $V_s$ differ in their relative response characteristics to oil and to contaminants. Calculating the oil concentration, from the calibration equations, using firstly the direct signal only, then using the scatter only, gives two concentration values, if these values compare within limits then no contaminant is present. If, however, they differ then contaminant is present and a correction factor related to the difference can be applied to one of the values to compensate.

The magnitude of the calibrated direct and scatter signals will drift over a period of time due to laser output variations, degradation of cell windows etc. To compensate for this effect the system is normalized at regular intervals. This consists of comparing the direct signal obtained with clean water to a reference value and calculating a multiplication factor to normalized the readings to this reference value. The direct and scatter readings are then multiplied by this normalizing factor. This may be done by multiplying the D1 and S1 constants in equations 1 and 2 below rather than performing a floating point multiplication on every reading.

Figure 5:
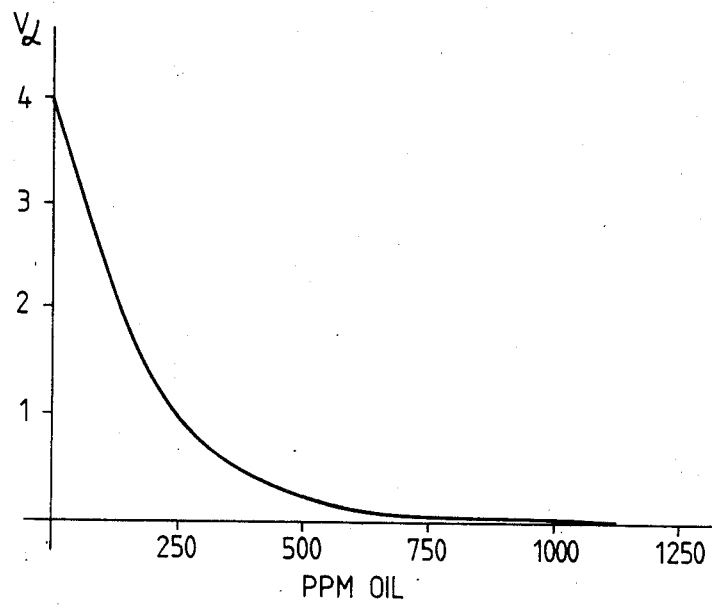
FIGS. 5 and 6 illustrate the response of the cell of FIGS. 1 and 2 to the presence of oil droplets after signal processing.
Figure 6:
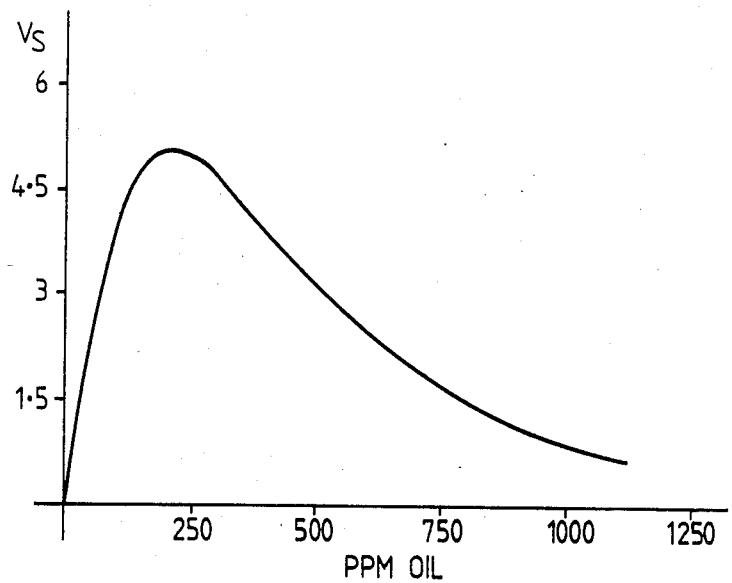

Theoretically two equations define the response of the system to oils:

The direct response is defined by $$V_d = D1 \times e^{-(D2 \times C)} \qquad \text{Eqn 1.}$$

and is of the form shown in FIG. 5. The scatter response is defined by $$V_s = S1 \times C \times e^{-(S2 \times C)} \qquad \text{Eqn 2.}$$

and is of the form in FIG. 6.

$V_d$ = Direct voltage.
$V_s$ = Scatter voltage.
C = Oil concentration in ppm.

D1, D2, S1, S2 are constants which vary slightly from installation to installation. D1 and S1 define the maximum values of the responses.

Equations 1 and 2 can be solved for C if the other coefficients are known thus each constant has to be calculated during calibration. This is achieved by injecting known amounts of oil into the sampled water and substituting the results into the equations. Both sets of constants can then be found by solving the equations 1 and 2 simultaneously.

Whilst the system is sampling, the direct and scatter signals $V_d$ and $V_s$ are continually converted into two oil concentrations by using Eqns 1 and 2.

The direct equation is directly solvable for C (giving the direct concentration value: D ppm). The scatter equation may be solved by an iterative method using an algorithm that converges on the final value (Scatter concentration value: S_ppm) with the minimum of iterations.

D_ppm and S_ppm are compared. If they are within a predetermined limit of each other then substantially no contaminant is present and the correct oil concentration is given by D_ppm. If the difference is greater than this limit then contaminant is assumed to be present and the D_ppm value must be compensated. The direct signal $V_d$ is generally more accurate than the scatter signal $V_s$ and thus, advantageously, it is used as the base for the calculations, the scatter signal being used as a check for the presence of contaminant and to calculate the correction factor required for D_ppm.

Calculating the compensation factor (in ppm) is performed by multiplying the scatter voltage error (S err) in millivolts by a value calculated from D_ppm (henceforth called D_cor) in ppm/mV. i.e.

$$CORRECT\ PPM = D\_ppm - (D\_cor \times S\_err) \qquad \text{Eqn 3.}$$

S_err is the voltage error difference between the actual voltage obtained and the voltage obtained by substituting D_ppm for C in equation 2.

The equation for D_cor has been derived from experimental results to slightly undercompensate for contaminent and is of the form:

$$D\_cor = M \times D\_ppm + C \qquad \text{Eqn 4.}$$

i.e. a linear relationship where M & C are constants.

It should be noted that different types of oil, e.g. arabian light and Nigerian medium, have different calibrated scatter responses above about 150 ppm, i.e. when the effect of absorption begins to dominate over scattering. Thus it is possible to calibrate for one type of oil only and the algorithm will work over the whole range for that one oil or by selecting a typical calibration, say for arabian light, and restricting the range of the algorithm to below approx 150 ppm then the algorithm will discriminate contaminant for a range of oils with similar characteristics to arabian light, i.e. oils defined as black oils. Above 150 ppm the effect of contaminant may be reduced by using an homogenizer to increase the system's response to oil in preference to contaminant.

The two groups of oils, black and white, will require separate calibrations since both direct and scatter calibration responses differ between the qroups. The correct calibration will be selected by the operator when the system is sampling.

A schematic diagram of an apparatus for performing the signal processing is shown in FIG. 7. The direct and scatter outputs from the cell 51 are fed respectively to first and second amplifiers 52 and 53 whereby the output signals $V_d$ and $V_s$ corresponding to the measured oil levels are generated. The two signals are then fed e.g. to a microprocessor 54 which performs the computation previously described thereby devising a compensation factor. Typically this correction factor is then applied to the $V_d$ signal to give a true measure of the oil concentration. The two signals are compared by comparator 55, the output of which is coupled to subtractor 56. The comparator output provides a measure of the difference between the direct and scatter signals. This difference signal is applied to subtractor 56 whereby the difference is subtracted from the scatter signal, the subtract and being fed to output O/P to provide a measure of the oil concentration.

We claim:

1. A method of detecting and measuring oil dispersed in water, the method including directing a substantially monochromatic light beam through an oil/water mixture, measuring the relative intensities of light transmitted directly through the mixture and scattered at an angle to the incident beam, and normalizing the direct and transmitted output signals by multiplying said signals by respective first and second predetermined multiplication factors, comparing the two normalized output signals, and subtracting from the normalized scatter output signal a further factor proportional to the difference between the two normalized output signals thereby obtaining a measure of the oil concentration in the mixture.

2. A method of detecting and measuring oil in water, the method including directing a substantially monochromatic light beam through an oil/water mixture to first and second photovoltaic detectors disposed respectively in line with and at an angle to the light beam so as to receive light transmitted directly and via a scatter path through the mixture, amplifying the outputs of the detectors, determining from the relative values of the detector outputs a factor corresponding to non-oleus contamination in the oil/water mixture, and applying the factor to the signal derived from the direct light path so as to provide a measure of the oil concentration in the mixture.

3. An apparatus for detecting and measuring oil in water, the apparatus including a cell through which an oil/water mixture may be directed, means for directing a substantially monochromatic light beam through the cell, means for detecting the intensity of light transmitted via direct and scatter paths through the cell and for generating voltage signals corresponding to said intensities, and means for calculating from said voltages a correction factor corresponding to the level of non-oleus contamination in the oil water mixture and for applying said factor to the direct path voltage signal thereby providing a measure of the oil concentration in the mixture.

4. An apparatus as claimed in claim 3, wherein said calculating means includes a microprocessor.

* * * * *